(12) United States Patent
Heesch et al.

(10) Patent No.: US 8,677,991 B2
(45) Date of Patent: Mar. 25, 2014

(54) RESPIRATOR

(75) Inventors: Ralf Heesch, Lübeck (DE); Andreas Brandt, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 563 days.

(21) Appl. No.: 13/044,115

(22) Filed: Mar. 9, 2011

(65) Prior Publication Data

US 2011/0247614 A1  Oct. 13, 2011

(30) Foreign Application Priority Data

Apr. 9, 2010  (EP) .................................... 10159449

(51) Int. Cl.
*A61M 16/12* (2006.01)
*A61M 16/20* (2006.01)
*A61M 16/01* (2006.01)

(52) U.S. Cl.
USPC ................................ 128/203.12; 128/205.24

(58) Field of Classification Search
CPC ...................................................... A61M 16/10
USPC .............. 128/203.12, 203.14–17, 203.25–27, 128/204.18, 204.21, 204.22, 205.11, 128/205.24; 137/88; 366/182.4
See application file for complete search history.

(56) References Cited

U.S. PATENT DOCUMENTS

| 4,023,587 A | 5/1977 | Dobritz |
| 5,383,449 A | 1/1995 | Forare et al. |
| 5,915,834 A | 6/1999 | McCulloh |

FOREIGN PATENT DOCUMENTS

| CN | 101 36 5510 A | | 2/2009 |
| CN | 103122456 A | * | 11/2013 |
| WO | WO 9829154 Al | | 7/1998 |
| WO | WO 2007064986 A2 | | 6/2007 |

* cited by examiner

*Primary Examiner* — Jackie Ho
*Assistant Examiner* — Mark Wardas
(74) *Attorney, Agent, or Firm* — McGlew and Tuttle, P.C.

(57) ABSTRACT

A respirator or anesthesia apparatus, for the artificial respiration of a patient, has a gas delivery device, at least one gas line for forming a breathing air line system, at least one gas mixing means with a mixed gas tank and at least two inlet openings with a shut-off member each for separately feeding at least two different gases to be mixed into the mixed gas tank and for subsequently feeding the mixed gas into the breathing air line system. The mixed gas tank is provided with at least two separate outlet openings for releasing the mixed gas from the mixed gas tank and for subsequently feeding it into the breathing air line system.

20 Claims, 1 Drawing Sheet

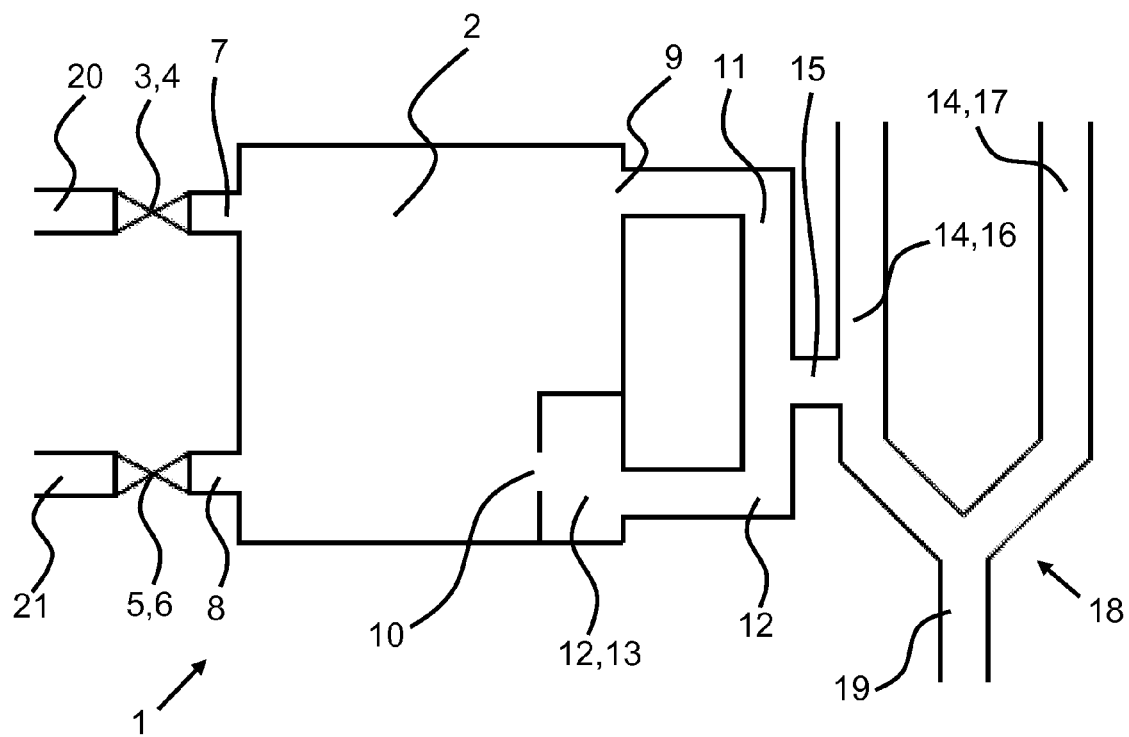

RESPIRATOR

CROSS REFERENCE TO RELATED APPLICATIONS

This application claims the benefit of priority under 35 U.S.C. §119 of European Patent Application EP 10 159 449.7 filed Apr. 9, 2010, the entire contents of which are incorporated herein by reference.

FIELD OF THE INVENTION

The present invention pertains to a respirator (also known as a ventilator) or anesthesia apparatus for artificial respiration (also known as a ventilation) of a patient comprising a gas delivery means, at least one gas line for forming a breathing air line system such as a breathing air circulation system, at least one gas mixing means with a mixed gas tank and at least two inlet openings with a shut-off member each for separately feeding at least two different gases to be mixed into the mixed gas tank and for subsequently feeding the mixed gas into the breathing air line system and to a process of mixing at least two different gases in the respirator or anesthesia apparatus.

BACKGROUND OF THE INVENTION

Artificial respiration of patients is necessary for various medical applications, e.g., during surgical procedures. Respirators are used for the artificial respiration of patients and may additionally also be used as anesthesia apparatuses for anesthesia with an anesthetic reflector and anesthetic dispensing unit. The expiration gas expired by the patient can be reused at least partly in some respirators, i.e., these devices represent a rebreathing system with a breathing air circulating system. A gas delivery means, which sends the breathing air to the patient during the inspiration, is present in the respirator with the breathing air circulating system. The gas delivery means is either switched off or is operated with a very low delivery flow only during and after the expiration.

It is necessary, especially in anesthesia apparatuses, to feed a mixed gas to the inspiration gas. The mixed gas consists, for example, of oxygen and laughing gas. The gases to be mixed, namely, oxygen and laughing gas, are fed separately through shut-off valves to a mixed gas tank. The gases to be mixed, for example, oxygen or laughing gas, are introduced intermittently, such that only one shut-off valve is alternatingly opened. Thus, either, for example, only oxygen or only laughing gas is fed to the mixed gas tank. The mixed gas is released from the mixed gas tank continuously into a breathing air line system, especially into an inspiration gas line. If a gas to be mixed, for example, oxygen, is introduced into the mixed gas tank, the concentration of oxygen increases in the mixed gas tank, because only oxygen is introduced into the mixed gas tank. This also applies analogously if, for example, only laughing gas is introduced into the mixed gas tank. The mixed gas is released from the mixed gas tank continuously. The mixed gas removed from the mixed gas tank is fed to a breathing air line system of a respirator or anesthesia apparatus. Fluctuations in concentration will occur in the mixed gas tank and hence also in the mixed gas, which is fed to the breathing air line system, because of the intermittent dispensing. However, these fluctuations in concentration are not desirable, because the inspiration gas fed to the patient shall have the most uniform concentration possible.

Local fluctuations in concentration may also occur within the mixed gas tank, so that additional fluctuations may likewise also occur in the concentration of the mixed gas fed to the breathing air line system as a result because of a non-optimal mixing of the mixed gas in the mixed gas tank.

SUMMARY OF THE INVENTION

The object of the present invention is therefore to make available a respirator or anesthesia apparatus and a process for mixing at last two different gases in a respirator and anesthesia apparatus, in which fluctuations in the concentration of a mixed gas introduced into a breathing air line system can be compensated in a simple and reliable manner with a small technical effort.

This object is accomplished with a respirator or anesthesia apparatus for the artificial respiration of a patient, comprising a gas delivery means, at least one gas line for forming a breathing air line system, especially a breathing air circulation system, at least one gas mixing means with a mixed gas tank and at least two inlet openings with a shut-off means each for the separate feed of at least two different gases to be mixed, especially oxygen, laughing gas, air, carbon dioxide or xenon, into the mixed gas tank and for the subsequent feeding of the mixed gas from the mixed gas tank into the breathing air line system, wherein the mixed gas tank is provided with at least two separate outlet openings for releasing the mixed gas from the mixed gas tank and for subsequently feeding it into the breathing air line system. Based on the release of the mixed gas from the mixed gas tank from at least two separate outlet openings, local fluctuations in concentration within the mixed gas tank can be compensated.

In an additional embodiment, the at least two separate outlet openings in the mixed gas tank have a distance of at least 1 cm, 2 cm, 5 cm, 7 cm or 10 cm.

In particular, a mixed gas line each is arranged at the at least two outlet openings, so that the mixed gas released from the at least two outlet openings flows through at least two mixed gas lines before being introduced into the breathing air line system.

The at least two mixed gas lines open into a mixed gas collection line and the mixed gas collection line opens into the breathing air line system in another embodiment. Additional mixing of the gases of the mixed gas can take place in the mixed gas collection line.

In an additional embodiment, the at least two mixed gas lines have different volumes for a pneumatic time delay between the at least two outlet openings and the breathing air line system and/or the mixed gas collection line. Fluctuations in the concentration of the gases to be mixed, which are fed to the mixed gas tank, occur within the mixed gas in the mixed gas tank. Only one gas to be mixed is fed now alternatingly to the mixed gas tank, so that fluctuations will occur in the concentration in the mixed gas in the mixed gas tank. Fluctuations in the concentrations of the different gases to be mixed, which are fed into the mixed gas tank, can be essentially compensated by a pneumatic time delay of the mixed gas taken from the at least two outlet openings. If, for example, a first gas to be mixed is present at a maximum concentration in the mixed gas tank at a first point in time and a second gas to be mixed is present in the mixed gas tank at a maximum concentration at a second point in time, the pneumatic time delay corresponds essentially to the time difference between the first and second points in time. The first gas to be mixed is present during the second point in time at a minimum concentration in the mixed gas tank. For example, the gas, which was removed from the mixed gas tank during the first point in time, is mixed with the mixed gas, which was removed from the mixed gas tank during the second point in time. As a result, mixed gas with a maximum concentration of the second gas to be mixed is mixed with mixed gas, which has a maximum concentration of the first gas to be mixed. As a result, the fluctuations occurring in the concentrations in the mixed gas tank can be essentially compensated in respect to the mixed gas fed to the breathing air line system based on the continuously increasing and decreasing fluctuations in the concentrations of the first and second gases to be mixed in the mixed gas tank.

The volume of at least one mixed gas line is preferably larger than the volume of another mixed gas line by a factor of 1.1, 1.5, 2, 3 or 5.

In one variant, the gases to be mixed, which are introduced into the mixed gas tank through the at least two inlet openings with a shut-off member each, can be introduced intermittently into the mixed gas tank.

The shut-off members are preferably controlled such that only one shut-off member is alternatingly opened.

In another embodiment, the difference of the volumes of at least two mixed gas lines corresponds essentially to a deviation of less than 70%, 50%, 30% or 20% of the volume of the mixed gas, which flows through the outlet opening arranged at the mixed gas line with the larger volume during an opening time of a shut-off member.

In particular, at least one mixed gas line is arranged at least partially, especially as a buffer tank, within the mixed gas tank. The at least one mixed gas line with the larger volume can thus be made compact, because this is integrated as a result in the mixed gas tank as a buffer tank and the gas mixing means as a whole thus has a compact design.

A process is provided according to the present invention for mixing at least two different gases in a respirator or anesthesia apparatus, especially a respirator or anesthesia apparatus described in this patent application, with the steps of introducing at least two gases to be mixed into a mixed gas tank, mixing of the at least two gases in the mixed gas tank, releasing the mixed gas from the mixed gas tank, introduction of the mixed gas into a breathing air line system, wherein the mixed gas is released from the mixed gas tank separately at least two different outlet openings.

In another embodiment, the mixed gas released from an outlet opening is fed continuously with a time difference to the breathing air line system in relation to the mixed gas that is released from another outlet opening and is fed to the breathing air line system.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

BRIEF DESCRIPTION OF THE DRAWING

In the drawing:
FIG. 1 is a simplified view of a gas mixing means.

DESCRIPTION OF THE PREFERRED EMBODIMENTS

Referring to the drawings in particular, FIG. 1 shows a gas mixing means 1 of an anesthesia apparatus, not shown.

The anesthesia apparatus has a breathing air circulation system, so that expiration gas expired by the patient can be reused at least partly as an inspiration gas. The anesthesia apparatus is thus used for the artificial respiration and for the anesthesia of a patient, not shown.

The inspiration gas fed to patients to be respirated is fed to the patient through an inspiration gas line 16, which is designed as a part of a breathing air line system 14, especially as a breathing air circulation system here. After flowing through the inspiration gas line 16 and a Y-piece 18, the inspiration gas is fed to the patient through a mouthpiece 19. The air expired by the patient is drawn off as expiration gas through an expiration gas line 17. Nonreturn valves, not shown, are arranged at each of the inspiration gas as well as expiration gas lines 16, 17.

A mixed gas collection line 15 opens into the inspiration gas line 16. Mixed gas consisting of different gases, for example, oxygen and laughing gas, is fed to the inspiration gas for the patient to be respirated through the mixed gas line 15. The gas mixing means 1, which makes the mixed gas available, which said mixed gas is introduced into the inspiration gas line 16 through the mixed gas collection line 15, has a mixed gas tank 2 with a first inlet opening 7 and a second inlet opening 8. A first shut-off member 3, for example, a shut-off valve 4 or a gate valve, is arranged at the first inlet opening 7, and a second shut-off member 5, for example, a second shut-off valve 6 or a second gate valve, is arranged at the second inlet opening 8. A first gas to be mixed, e.g., oxygen, is introduced into the mixed gas tank 2 through a first feed line 20, and a second gas to be mixed, e.g., laughing gas, is introduced into the mixed gas tank 2 through a second feed line 21. The first shut-off member 3 and the second shut-off member 5 are opened now alternatingly, so that only oxygen flows into the mixed gas tank 2 through the first feed line 7 during a first time period and only laughing gas flows into the mixed gas tank 2 through the second inlet opening 8 during a second time period. The two shut-off members 3, 5 are thus not opened simultaneously.

The mixed gas tank 2 has a first outlet opening 9 and a second outlet opening 10. The gas mixed in the mixed gas tank is removed from the mixed gas tank 2 through the first and second outlet openings 9, 10. The two outlet openings 9, 10 are spaced apart a greater distance, for example, in the range of 1 cm to 10 cm. The mixed gas removed from the first outlet opening 9 is fed through a first mixed gas line 11 to the mixed gas collection line 15 and the mixed gas removed from the second outlet opening 10 is likewise sent to the mixed gas collection line through a second mixed gas line 12. The second mixed gas line 12 is partly also integrated in the mixed gas tank 2 and has a substantially larger volume than the first mixed gas line 11. The second mixed gas line 12 in the mixed gas tank 2 is designed here as a buffer tank 13, at which the second outlet opening 10 is also present. Due to the separate removal of the mixed gas from the mixed gas tank through two different outlet openings 9, 10, local fluctuations in the oxygen and laughing gas concentrations within the mixed gas tank 2 can advantageously be essentially compensated.

Due to the intermittent and alternating introduction of the two gases to be mixed into the mixed gas tank 1, fluctuations will occur in the concentrations of the two gases oxygen and laughing gas in the mixed gas. If, for example, only oxygen is introduced into the mixed gas tank 2 through the first shut-off member 3 and the first inlet opening 7, the concentration of oxygen increases in the mixed gas tank 2 and the concentration of laughing gas will also decrease as a result in the mixed gas tank 2. The mixed gas is now released continuously from the mixed gas tank 2 through the two outlet openings 9, 10 and introduced continuously into the inspiration gas line 16. The volume of the second mixed gas line 12 with the buffer tank 13 is substantially larger than the volume of the first mixed gas line 11. This leads to a pneumatic time delay of the mixed gas, which flows into the mixed gas collection line 15 through the first and second mixed gas lines 11, 12. The difference of the volumes between the first and second mixed gas lines 11, 12 is designed such that the mixed gas sent through the first mixed gas line 11 to the mixed gas collection line 15 has a maximum oxygen concentration and the mixed gas introduced at the same point in time into the mixed gas collection line 15 through the second mixed gas line 12 has a maximum laughing gas concentration. Due to the larger volume of the second mixed gas line 12, the mixed gas, which is removed from the mixed gas tank 2 through the second mixed gas line 12 and is introduced into the mixed gas collection line 12, thus flows into the mixed gas collection line 15 with a time delay in relation to the mixed gas that is introduced into the mixed gas collection line 15 through the first mixed gas line 11. At a maximum oxygen concentration in the mixed gas tank 2, a minimum concentration of laughing gas is present in the mixed gas tank 2 and vice versa. The concentration of oxygen in the mixed gas tank 2 increases during the period during which only oxygen is fed exclusively into the mixed gas tank 2, and the concentration of laughing gas analogously decreases in the mixed gas tank 2. The concentration of laughing gas analogously increases continuously in the mixed gas tank 2 and the concentration of oxygen decreases in the mixed gas tank 2 during the period during which laughing gas is exclusively introduced into the mixed gas tank 2. If, for example, the oxygen concentration decreases and the laughing gas concentration increases in the mixed gas tank 2, this leads, because of the pneumatic time delay at the beginning of the mixed gas collection line 15, to a simultaneous increase in the concentration of oxygen in the mixed gas in the second mixed gas line 12, i.e., at the end of the second mixed gas line 12 at the mixed gas collection line 15 and an increase of the concentration of laughing gas in the mixed gas at the end of the first mixed gas line 11 at the mixed gas collection line 15. This is also true vice versa. The concentration fluctuations of the mixed gas in the mixed gas tank 2 due to the alternating and intermittent admission of the two gases to be mixed can thus be compensated in the mixed gas tank 2 continuously essentially in a simple manner.

On the whole, considerable advantages are associated with the respirator or anesthesia apparatus according to the present invention. The separate release of the mixed gas from the at least two separate outlet openings 9, 10 makes it possible to essentially compensate concentration fluctuations within the mixed gas tank 2 due to an inhomogeneous mixing of the mixed gas. The fluctuations in the concentration of the gases to be mixed in the mixed gas tank 2 over time can be essentially compensated by the pneumatic time delay in the two mixed gas lines 11, 12. This makes possible an essentially constant concentration of the mixed gas fed to the inspiration gas line 16.

While specific embodiments of the invention have been shown and described in detail to illustrate the application of the principles of the invention, it will be understood that the invention may be embodied otherwise without departing from such principles.

LIST OF REFERENCE NUMBERS

1 Gas mixing means
2 Mixed gas tank
3 First shut-off member
4 First shut-off valve
5 Second shut-off member
6 Second shut-off valve
7 First inlet opening
8 Second inlet opening
9 First outlet opening
10 Second outlet opening
11 First mixed gas line
12 Second mixed gas line
13 Buffer tank
14 Breathing air line system
15 Mixed gas collection line
16 Inspiration gas line
17 Expiration gas line
18 Y-piece
19 Mouthpiece
20 First feed line for the first gas to be mixed
21 Second feed line for the second gas to be mixed

What is claimed is:

1. A respirator or anesthesia apparatus for the artificial respiration of a patient, the respirator or anesthesia apparatus comprising:
a gas delivery means;
a breathing air line system including at least one gas line;
at least one gas mixing means with a mixed gas tank having at least two inlet openings, each of the inlet openings having a shut-off member for separately feeding at least two different gases to be mixed into the mixed gas tank to form a mixed gas and for subsequently feeding the mixed gas into the breathing air line system, the mixed gas tank having at least two separate outlet openings for releasing the mixed gas from the mixed gas tank and for subsequently feeding mixed gas from the mixed gas tank into the breathing air line system.

2. A respirator or anesthesia apparatus in accordance with claim 1, wherein a mixed gas line is arranged at each of the at least two outlet openings so that the mixed gas released from the at least two outlet openings flows through the at least two mixed gas lines before being introduced into the breathing air line system.

3. A respirator or anesthesia apparatus in accordance with claim 2, wherein the at least two mixed gas lines open into a mixed gas collection line and the mixed gas collection line opens into the breathing air line system.

4. A respirator or anesthesia apparatus in accordance with claim 2, wherein the at least two mixed gas lines have different volumes for a pneumatic time delay between the at least two outlet openings and the breathing air line system.

5. A respirator or anesthesia apparatus in accordance with claim 4, wherein the volume of at least one of the mixed gas lines is larger than the volume of another of the mixed gas lines by one of at least 1.1, 1.5, 2, 3 or 5 times.

6. A respirator or anesthesia apparatus in accordance with claim 1, wherein the gases to be mixed, which are introduced into the mixed gas tank through the at least two inlet openings with the shut-off member each can be introduced into the mixed gas tank intermittently.

7. A respirator or anesthesia apparatus in accordance with claim 1, wherein the shut-off members are controlled such that only one shut-off member is alternatingly opened.

8. A respirator or anesthesia apparatus in accordance with claim 2, wherein:
there is a volume difference between the at least two mixed gas lines;
the difference of the volumes of the at least two mixed gas lines corresponds with a deviation of less than 70%, 50%, 30% or 20%, to the volume of the mixed gas, which flows during an opening time of one of the shut-off members through the outlet opening.

9. A respirator or anesthesia apparatus in accordance with claim 2, wherein at least one of the at least two mixed gas lines is arranged at least partly within the mixed gas tank to form a buffer tank.

10. A respirator or anesthesia apparatus in accordance with claim 3, wherein the at least two mixed gas lines have different volumes for a pneumatic time delay between the at least two outlet openings and the breathing air line system and/or the mixed gas collection line.

11. A process for mixing at least two different gases in a respirator or anesthesia apparatus, the process comprising the steps of:
providing a respirator or anesthesia apparatus with a gas delivery means, a breathing air line system including at least one gas line and at least one gas mixing means with a mixed gas tank having at least two inlet openings, each of the inlet openings having a shut-off member for separately feeding at least two different gases to be mixed into the mixed gas tank to form a mixed gas and for subsequently feeding the mixed gas into the breathing air line system, the mixed gas tank having at least two separate outlet openings for releasing the mixed gas from the mixed gas tank and for subsequently feeding mixed gas from the mixed gas tank into the breathing air line system;
introducing at least two gases to be mixed into a mixed gas tank;
mixing the at least two gases in the mixed gas tank;
releasing the mixed gas from the mixed gas tank;
introducing the mixed gas into the breathing air line system wherein the mixed gas is released from the mixed gas tank separately at the at least two separate outlet openings.

12. A process in accordance with claim 11, wherein the mixed gas released from one outlet opening of the at least two separate outlet openings is fed continuously to the breathing air line system with a time difference in relation to the mixed gas that is released from another outlet opening of the at least two separate outlet openings and fed to the breathing air line system.

13. A respirator or anesthesia apparatus for the artificial respiration of a patient, the respirator or anesthesia apparatus comprising: a breathing air line system including at least one gas line; a mixed gas tank having a first inlet opening and a second inlet opening and having a first outlet opening and a second outlet opening; a first shut-off member at the first inlet opening for separately feeding a gas to be mixed into the mixed gas tank via the first inlet opening; a second shut-off member at the second inlet opening for separately feeding a gas to be mixed into the mixed gas tank via the second inlet opening; a first mixed gas line connected to the first outlet opening and connected to the breathing air line system for releasing the mixed gas from the mixed gas tank into the breathing air line system; and a second mixed gas line connected to the second outlet opening and connected to the breathing air line system for releasing the mixed gas from the mixed gas tank into the breathing air line system.

14. A respirator or anesthesia apparatus in accordance with claim 13, wherein the at least two mixed gas lines have different volumes to provide a pneumatic time delay between mixed gas traveling from the first outlet opening to the breathing air line system and mixed gas traveling from the second outlet opening to the breathing air line system.

15. A respirator or anesthesia apparatus in accordance with claim 14, further comprising a mixed gas collection line, the first mixed gas line and the second mixed gas line being connected to the breathing air line system via the mixed gas collection line.

16. A respirator or anesthesia apparatus in accordance with claim 14, wherein the volume of at least one of the mixed gas lines is larger than the volume of another of the mixed gas lines by one of at least 1.1, 1.5, 2, 3 or 5 times.

17. A respirator or anesthesia apparatus in accordance with claim 14, wherein:
the first shut-off member and the second shut off member are controlled to open the first shut-off member while the second shut-off member is closed and to open the second shut off member while the first shut-off member is closed;
the gases to be mixed, which are introduced into the mixed gas tank through the first inlet opening and the second inlet opening with the first shut-off member and the second shut off member, are introduced into the mixed gas tank intermittently.

18. A respirator or anesthesia apparatus in accordance with claim 17, wherein: different volumes of the two mixed gas lines correspond to a deviation of a volume of gas which flows during an opening time of a shut-off member.

19. A respirator or anesthesia apparatus in accordance with claim 13, wherein at least one of the first mixed gas line and second mixed gas line is arranged at least partly within the mixed gas tank to form a buffer volume.

20. A respirator or anesthesia apparatus in accordance with claim 13, wherein the at least first mixed gas line and the second mixed gas line have different volumes for a pneumatic time delay between gas travel time from the first outlet opening to the breathing air line system and from the second outlet opening to the breathing air line system.

* * * * *